US006425758B1

(12) United States Patent
Förster (10) Patent No.: US 6,425,758 B1
(45) Date of Patent: Jul. 30, 2002

(54) FLEXIBLE SPRING BRACE FOR THE CORRECTION OF TOOTH MISALIGNMENT

(76) Inventor: Rolf Förster, Vogesenalle 58, D-75173 Pforzheim (DE)

( * ) Notice: Subject to any disclaimer, the term of this patent is extended or adjusted under 35 U.S.C. 154(b) by 0 days.

(21) Appl. No.: 09/162,624

(22) Filed: Sep. 29, 1998

(30) Foreign Application Priority Data

Sep. 29, 1997 (DE) ......................... 197 42 860

(51) Int. Cl.[7] ................................................ A61C 3/00
(52) U.S. Cl. ........................................................ 433/7
(58) Field of Search .............................. 433/7, 18, 20, 433/22, 21

(56) References Cited

U.S. PATENT DOCUMENTS 360,695 A  * 4/1887  Holmes ........................ 433/7
3,284,902 A  * 11/1966  Dillberg et al. ................ 433/7
4,571,178 A  * 2/1986  Rosenberg .................... 433/7
5,975,894 A  * 11/1999  Pozzi ........................... 433/7

* cited by examiner

Primary Examiner—Todd E. Manahan

(57) ABSTRACT

A elastic expansion appliance for correcting misalignments of teeth, which has two members connected by linear guidance element(s), a spacing between which can be modified via a spring arranged between them, wherein in order to adjust the distance over which the spacing of the two members can be modified, a stop of variable length (measured in the direction of the linear guidance elements) is provided for the spring or for a spring arrangement of more than one spring and/or for one of the two members.

33 Claims, 10 Drawing Sheets

FLEXIBLE SPRING BRACE FOR THE CORRECTION OF TOOTH MISALIGNMENT

The present invention is based on an elastic expansion appliance having the features indicated in the preamble of claim 1. An elastic expansion appliance of this kind is known from U.S. Pat. No. 5,167,500. The known elastic expansion appliance comprises two members joined to one another by two parallel guide rods, and a pseudoelastic coiled spring which is arranged between the two members. Each of the two guide rods is fastened at one of its ends in an orifice of one of the two members, and sits at its other end in a pertinent orifice of the opposing member, so that the two members can change the spacing between them by displacement along the two guide rods. The displacement can be effected by the coiled spring. The two members are intended either to be embedded in a plastic palate plate and/or to carry soldered-on or welded-on arms which respectively carry retention elements, clamps, or eyes which engage on teeth whose position is to be corrected, this occurring under the action of the spring. For this purpose, the elastic expansion appliance is installed into the dentition with the spring under stress, e.g. in the compressed state, and thereafter acts with the return force of the spring on the tooth or teeth whose position is to be corrected, the elastic expansion appliance being capable of expanding until the return force of the spring has declined to the point that it is no longer sufficient to correct tooth position. The magnitude of the correction which actually occurs thus results from the expansion which the spring performs until it has relaxed. If it is desired to change the magnitude of the correction, it is necessary either to change the distance ever which the elastic expansion appliance is initially compressed, and/or to replace the spring. Both are laborious and unsuitable for practical use. A further disadvantage is the fact that the preselected displacement travel is too great for the intended correction of the tooth position, which may become evident only in the course of the treatment. The physician performing the treatment can only ascertain this. However, if the patient comes in regularity for examination, it the patient does not do so, or does so ton late, the tooth position may already have been changed to such an extent that a countercorrection is necessary. This can be eliminated, however, by way of a jackscrew which is already disclosed in U.S. Pat. No. 5,167,500 as existing art and which displaces the two variable-spacing members not by way of a spring, but by way of a double spindle having sections threaded in opposite directions. In ardor to prevent excessive correction forces, a jackscrew of this kind can always be expanded by no more than 0.25 mm. For a typical tooth correction with 4 mm of tooth movement, the patient must therefore visit the doctor 16 times in order to have the jackscrew readjusted, which is laborious and tiresome. The came applies to the combined tension and compression screws according to Heller for sagittal movement of teeth.

An elastic jackscrew according to Hauser, disclosed in DE-824 632, allows for somewhat fewer readjustments than with a springless jackscrew. An elastic jackscrew of this kind is, however, more complex to manufacture than a springless (rigid) jackscrew.

It is the object of the present invention to indicate a way in which the progress of a tooth position correction can easily and reliably be kept under control.

This object is achieved by an elastic expansion appliance having the features indicated in claim 1. Advantageous developments of the invention are the subject of the dependent claims.

According to the present invention, in order to adjust the distance over which the spacing of the two members of the elastic expansion appliance can be changed, a stop of variable length is provided for the spring and/or for one of the two members, the length of the stop being measured in the direction of the linear guidance means. By way of such a stop, the distance over which the spring can relax, and thus the distance over which the spacing of the two members can change, can be changeably predefined. In this fashion, the physician performing the treatment can specifically define, by visual inspection, how much tooth correction is to occur until the first examination. There are no deleterious consequences even if the patient does not arrive for an agreed-upon examination appointment, since correction of the tooth position automatically ends when the preset distance has been reached.

In an advantageous development of the invention, the length of the stop can be changed only in steps. This has the advantage that the length of the steps can be selected so that on the one hand sufficient treatment progress is attained, and on the other hand the step is not so large that an excessive, incorrect change in tooth position might occur. Misadjustments can be prevented by suitably selecting the step length. In the simplest case, the length of the stops can be changed in equal steps. It is also possible, however to conFig. the stops so that they can be changed in steps of unequal length. This has the particular advantage that longer steps can be set at the beginning of the treatment, while as the end of the treatment approaches, a shorter length can be selected for the steps; as a result, the treatment duration and the number of examinations can he decreased.

In an advantageous development of the invention, in order to constitute a stop that can be changed only in steps, provision is made for a stack of spacers, in particular plate-shaped, which are provided between the spring and one of the members, or between one of the members and an immovable stop. The spacers con easily be placed onto the linear guidance means which advantageously are guide rods, optimally perpendicular to the longitudinal direction of the linear guidance means, since they can then be removed without disassembling the elastic expansion appliance or destroying the spacers. In order to allow the spacers to be placed onto the linear guidance means perpendicular to their longitudinal direction, they advantageously have a laterally open recess into which the linear guidance means engage. This laterally open recess can be a slot into which the linear guidance means are inserted, one after another, when the spacers are slid onto the two linear guidance means in the direction of the plane spanned by said means. The spacers can also, however, be slid into the linear guidance means perpendicular to the plane spanned by said means, if the spacers have two slots provided at the spacing of the linear guidance means. Instead, however, it would also be possible to provide half-round recesses at opposite ends of the plate-shaped spacers, and clamp them with the recesses only between the linear guidance means. To ensure that they are securely held on the linear guidance means, they are advantageously snapped on, which is easily possible due to the inherent elasticity of a plate-shaped and, in particular, slotted spacer.

If the spacers are arranged between the spring and one of the members, then as the thickness of the spacer stank increases, given a predefined initial spacing between the two members, the stress on the spring becomes greater, and the distance over which the elastic expansion appliance expands in the course of the treatment is greater. If, on the other hand, the spacer stack is arranged riot between the spring and one of the members but between the member and an outer immovable stop, then as the thickness of the spacer packet increases the spring is also compressed more strongly, but at the same time the possible displacement travel is also limited. In this case, the elastic expansion appliance is used in such a way that at the beginning of the tooth correction the two members have a smaller spacing than would he determined by the spacers being used, i.e. at the beginning of the treatment, the member adjacent to the spacers is not in contact against the spacer stack, but rather is brought closer to the other member against the spring force, so that the possible expansion distance is determined by the spacing between the member adjacent to the spacers and the spacer stack. Tooth correction comes to a halt when the aforesaid member comes into contact against the spacer stack. The change in tooth position achieved up to that point can then be checked by the physician performing the treatment, and the treatment can easily be continued by removing one of the spacers from the spacer stack and thereby enabling a further expansion step, at the end of which the progress of the treatment can once again be checked. This procedure just described is particularly advantageous, which is why it is preferred to arrange the variable-length stop not between the spring and one of the members, but rather between the member and an outer immovable stop. With the configuration of the elastic expansion appliance, the physician performing the treatment has a choice between different procedures. For example, he or she might at the outset remove all the spacers, and thereby allow from the outset the maximum displacement travel of the elastic expansion appliance. He or she could also, however, always remove only one of the spacers, in order to check the tooth correction status after each step. He or she could also initially remove two or three spacers so as to begin with a large correction step and then complete the correction in shorter individual steps. He or she even has the possibility of leaving it to the patient, according to a predefined schedule, to remove individual spacers which for this purpose, especially if they are of different thicknesses are marked in distinguishable fashion, e.g. by being differently colored. The removal of spacers is extremely easy for the patient: to do so, he or she can release the apparatus, of which the elastic expansion appliance is a constituent, from the dentition by gently compressing the elastic expansion appliance, and remove it from his or her mouth. He or she can then, in accordance with instructions provided by the physician performing the treatment, remove a spacer and their reinsert the apparatus back into the dentition in the same fashion. Misadjustments can be practically ruled out, since the treatment steps are predefined by the thickness of the spacer.

The elastic expansion appliance is particularly advantageous if what is used as the spring, which advantageously is conFIG.d as a coiled spring, is not a conventional steel spring but rather a spring made of a shape-memory alloy which is pseudoelastic at the temperatures prevailing in the mouth. Preferred shape-memory alloys are alloys based on nickel and titanium, which contain nickel and titanium in approximately equal atomic percentages. Alloys of this kind can exist, depending on the temperature selected, in either the austenitic or martensitic state. Martensite is present at lower temperatures, austenite at higher temperature. The temperature at which the alloy begins to convert from austenite to martensite during cooling is called the Ms point. In the martensitic state below the Ms point, alloys of this kind can exhibit shape memory: a plastic deformation that has occurred in the martensitic state can be reversed by heating to a temperature above the Ms point, in a temperature range just above the Ms point, a shape-memory alloy of this kind can exhibit pseudoelastic behavior. This pseudoelastic behavior, sometimes also called "superelasticity," is characterized by the tact that the force required for increasing elongation of the material initially rises sharply as in the case of an austenite, but then, after reaching en elongation of approximately 1% to 2%, increases only slightly as elongation progresses further, and does not increase steeply again until reaching greater elongations of 6% to 8%. The intermediate elongation region is called the "martensite plateau," the name deriving from the fact that martensite forms in the alloy in response to the tensile stress. When the tension on the materiel is released, it reverts to the austenitic state. These pseudoelastic elongations are highly reversible up to elongations of more than 6% to 8%. Because of the pronounced martensite plateau, pseudoelasticity does not obey Hooke's law. Spring which exhibit this kind of pseudoelastic behavior are thus particularly suitable for the purposes of the present invention, since for spring travels in the region of the martensite plateau, the return force of the spring is almost independent of spring travel.

An elastic expansion appliance according to the invention thus has the great advantage that the pressure or tension exerted by the spring or the tooth remains almost unchanged for the duration of the treatment. Because the pressure or tension remains constant, the tooth position is changed more quickly then before. Since there is almost no change in spring force within the martensite plateau, it is moreover possible, by applying the invention, to reliably prevent excessive forces from inadvertently being set. The use of a pseudoelastic spring additionally makes it possible to define the step lengths by which the stop can be changed solely on the basis of the intervals at which an examination is desirable. There is no restriction on the step length for technical reasons, in contrast to elastic jackscrews with ordinarily elastic springs, in which the force exerted on the tooth increases in proportion to the step length and must be limited in order to prevent deleterious pressure spikes, and very much in contrast to jackscrews without springs, which in order to prevent deleterious pressure spikes should not be adjusted by more than 0.25 mm per step.

In the case of elastic expansion appliances according in the present invention having pseudoelastic springs, the selected step length by which the stop length can be modified is preferably between 0.75 mm and 1.25 mm, in particular 1 mm. In the majority of treatment instances, it is then possible to use only four treatment steps, end no more than four physician examinations. In contrast to the existing art with springless jackscrews which requite approximately four times as many treatment steps and physician examinations.

In the case of the elastic expansion according to the present invention, the spring can be arranged between the two members of the elastic expansion appliance in such a way that it attempts to increase the spacing between the two members. It is advantageous that the spring can, however, also be arranged so that it attempts to decrease the spacing between the two members. In this case the elastic expansion appliance experiences a negative expansion as the treatment progresses. Particularly suitable therefor is an arrangement of the spring in which it is retained in the one member between a stop provided immovably on that member and a stop that is displaceable in that member, the immovable stop being located closer to the other member than the displaceable stop, and the displaceable stop being joined to the other member via a tie rod. With this arrangement, the spring, initially loaded by compression, pulls the other member by way of the tie rod toward the one member as the tooth treatment progresses. In this context, the spring is preferably arranged so that it surrounds the tie rod, thus achieving a particularly compact configuration for the elastic expansion apparatus. A compact design is also promoted by a development of the invention according to which the spring is located in a cage which is mounted immovably on one member and projects beyond that one member toward the other member, which has a recess into which the projecting part of the cage can be introduced as the members approach one another. This cage, which is preferably a cylindrical sleeve, has the further advantage that it shields the spring and counteracts any deposition of food residues on the spring.

In another embodiment of the invention, there are provided in the elastic expansion appliance, instead of plate-shaped spacers, rod-shaped spacers which are arranged between linear guidance means in one of the members and extend perpendicular to the linear guidance means, so that they can he slid out of the elastic expansion appliance in their longitudinal direction. This embodiment also allows a very compact, space-saving design for the elastic expansion appliance, especially if the rod-shaped spacers do not project beyond the member in which they are arranged.

The rod-shaped spacers are intended, in this context, to rest against one another at their enveloping surfaces. For this purpose, they can be conFIG.d as rods with a rectangular cross section; in this case they can be guided against one another with their flat enveloping surfaces at which they touch one another. The rod-shaped spacers can also, however, be cylindrical. In order to be able to constitute a stable stack with cylindrical spacers, it is recommended that particular guidance means and/or holding means be provided in the member in which the cylindrical rods are arranged. For this purpose, the rod-shaped spacers in the one member are preferably arranged in a recess in which the guidance means and/or holding means which hold the spacers in their selected orientation are provided. These guidance means and/or holding means can be the wall which delimits the recess. It is also possible, however, to provide in the recess separate guidance means and/or holding means which perform this task alone or in combination with the wall of the recess. It is particularly advantageous to provide in the recess a shackle with which the spacers are held and guided linearly in the recess; this shackle is displaceable in the one member, and fastened in the other member. The shackle pulls the spacers, in response to one or more, preferably two springs, toward the other member of the elastic expansion appliance. When one of the spacers is removed, the spacing between the two members can be increased by the thickness of the rod-shaped spacer.

For good guidance and retention of the rod-shaped spacers in the recess of the one member, the shackle is preferably U-shaped, the two ends of the shackle being fastened in the other member of the elastic expansion appliance.

In order to be able to hold the rod-shaped spacers in the shackle, the spacers are preferably equipped with a constriction at which they snap in between the two arms of the shackle. The shackle is advantageously arranged in the recess with some lateral clearance, so that it can be elastically widened. This makes it easier, simply via pressure in their longitudinal direction, to snap the rod shaped spacers into piece and then release them from the snapped in position and slide them out of the elastic expansion appliance.

Preferably the recess is sealed except for two holes which are required for passage of the ends of the shackle, and with the exception of two aligned holes which are located above that rod-shaped spacer which is located in each case at the end wall of the recess which is adjacent to the other member of the elastic expansion appliance. Only the particular rod-shaped spacer located at this point can then he pushed nut of the elastic expansion appliance. As a result of the expansion of the spring(s) which thereupon takes place, the next rod-shaped spacer is pushed into the axis of these two aligned holes. The spacer is thereby largely protected from food residues in the recess; if necessary, the holes above and below it can be closed off with stoppers.

A plastic is preferably used as the material for the adjustable-length stop, which is conFIG.d in particular as a plate stack or a row of rods.

The invention is not limited to changing the stop only in steps. According to another advantageous development, the stop is made of a material which dissolves or decomposes in the mouth, so that the length of the stop automatically becomes shorter in the mouth, and a continuous adaptation of the displacement travel of the elastic expansion appliance thus takes place as the treatment progress. Suitable materials for a stop of this kind are polyglycolides (PGA), polyactides (PLA), stereocopolymers of PLA, copolymers of PLA, and resorbable ceramic materials. Also possible are hyaluronic acid and mixtures of the aforesaid materials, as well as polydioxanone, polyhydroxybutyric acid, copolymers of polyhydroxybutyric acid and hydroxyvaleric acid, as well as succinic acid polyesters.

In order for gradually dissolving or decomposing stop of this kind to shorten in defined fashion, it is advantageously located in a sheath which is open only at one or both ends but not along its outside diameter, so that decomposition or dissolution of the material can occur only in a manner proceeding from one or both ends, but not from all sides. It is possible by selecting the length of the stop to define the maximum displacement travel, and by way of the type of materiel to define the rate at which it dissolves or decomposes.

Exemplary embodiments of the invention are depicted in the appended drawings. Identical parts or parts which correspond to one another are labeled in the various exemplifying embodiments with matching reference numbers

Figure 1:
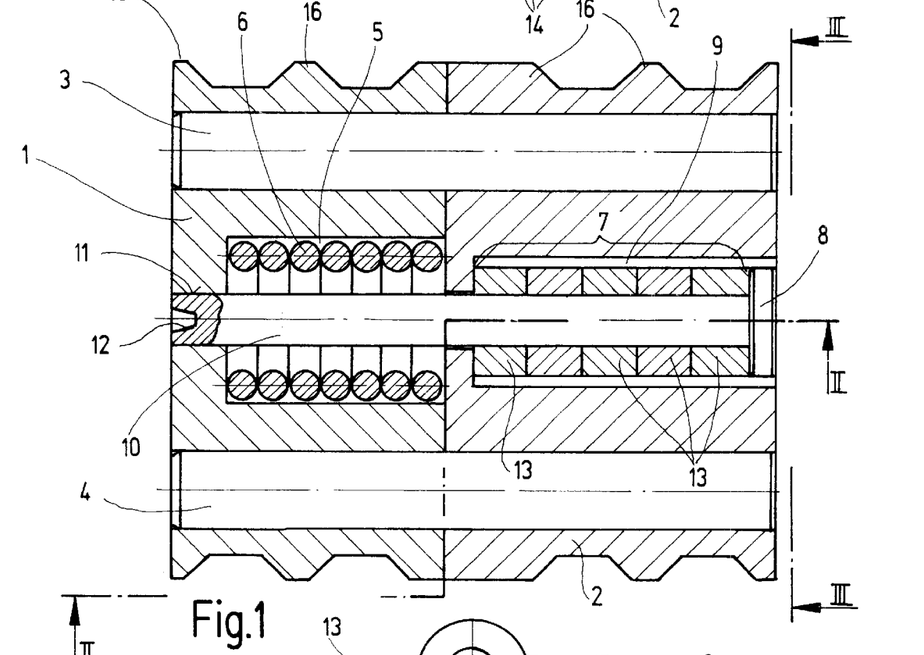
FIG. 1 shows an elastic expansion appliance for transverse movements, in horizontal section.
Figure 2:
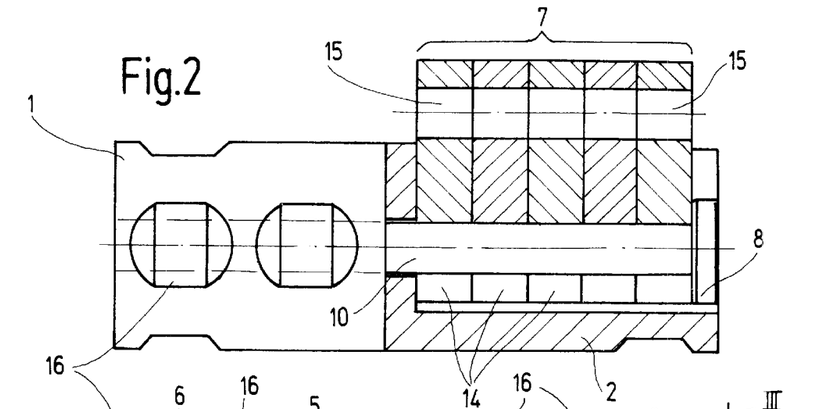
FIG. 2 shows the elastic expansion appliance of FIG. 1, half in side view and half in a vertical section along section line II—II.
Figure 3:
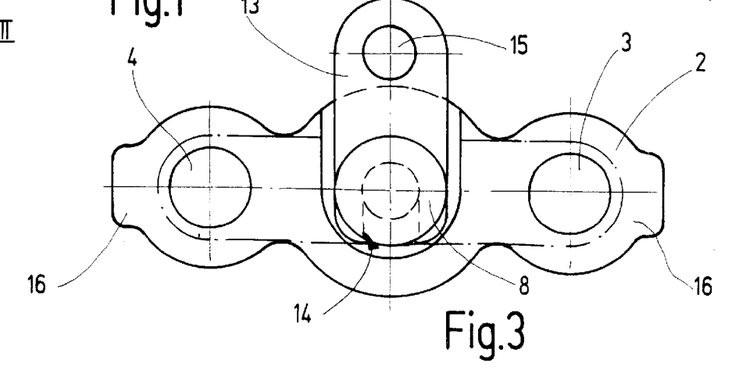
FIG. 3 shows view III—III of the elastic expansion appliance of FIG. 1.

The elastic expansion appliance depicted in FIGS. 1 through 3 contains a first member 1 and a second member 2, and guide rods 3 and 4 parallel to one another which connect ant members 1 and 2. For this purpose, member 1 contains two orifices, in which the two guide rods 3 and 4 are inserted and are fastened by calking. Second member 2 contains two orifices, aligning with the orifices in first member 1, into which guide rods 3 and 4 are inserted. First member 1 contains a central cylindrical recess 5 which is open toward second member 2 and receives a coiled spring 6 which exerts pressure on second member 2 and in that context is braced against the opposite bottom or recess 5. The compressive force exerted by spring 6 is absorbed by a stop 7 which is arranged between second member 2 and an externally located immovable stop 8, and lies in a recess 9 of second member 2. The immovable stop is located at the end of a centrally arranged tie rod 10 whose other end sits in an orifice 11 which extends from recess 5 to the outer end of first member 1. Tie rod 10 is fastened in orifice 11 by calking. FIG. 1 shows depression 12, resulting from the calking, in the end of tie rod 10.

Stop 7 comprises a stack of congruent, elongated plates 13 which have at their one end a slot 14 with which they can be placed from the side into opening 9 that is open at one end, and onto tie rod 10. At the opposite end, plates 13 each have a hole 15 which is located outside member 2. A pin can be introduced into holes 15, and plates 13 can be individually pulled out. When one of these plates is pulled nut, spring 6, which in FIG. 1 is completely compressed, can expand by a distance equal to the thickness of plate 13 that was pulled out, thus increasing the relative spacing of the two members 1 and 2 by that distance. Members 1 and 2 have on their outer sides retainers 16 so that they can be positively embedded into shaped elements (plates) made of cast resin, which in turn have clamps, eyes, or similar anchoring elements with which they can be anchored to the dentition, so as thereby to effect a tooth movement whose magnitude is determined by the number of plates pulled out.

Figure 4:
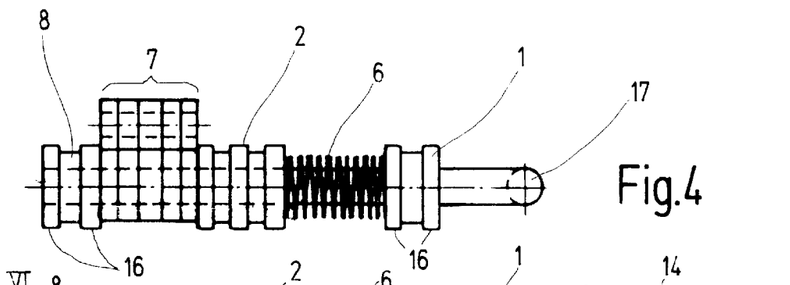
FIG. 4 shows a combined tension and compression elastic expansion appliance as a variant of a Heller jackscrew, in a side view.
Figure 5:
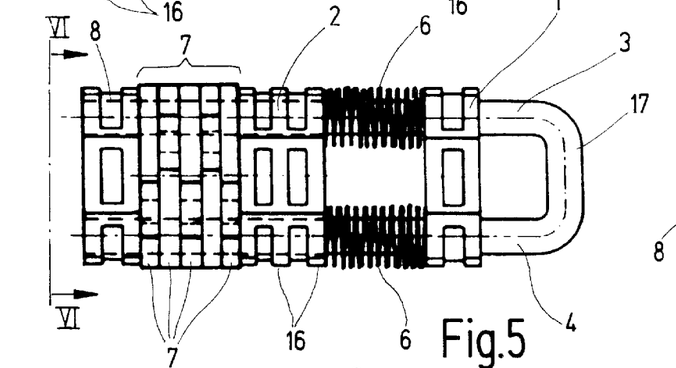
FIG. 5 shows the elastic expansion appliance of FIG. 4 in a plan view.
Figure 6:
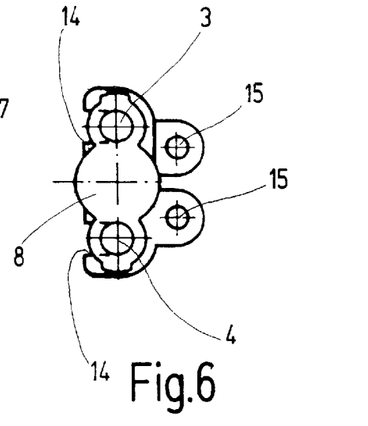
FIG. 6 shows view VI of the elastic expansion appliance of FIG. 5.
Figure 8:
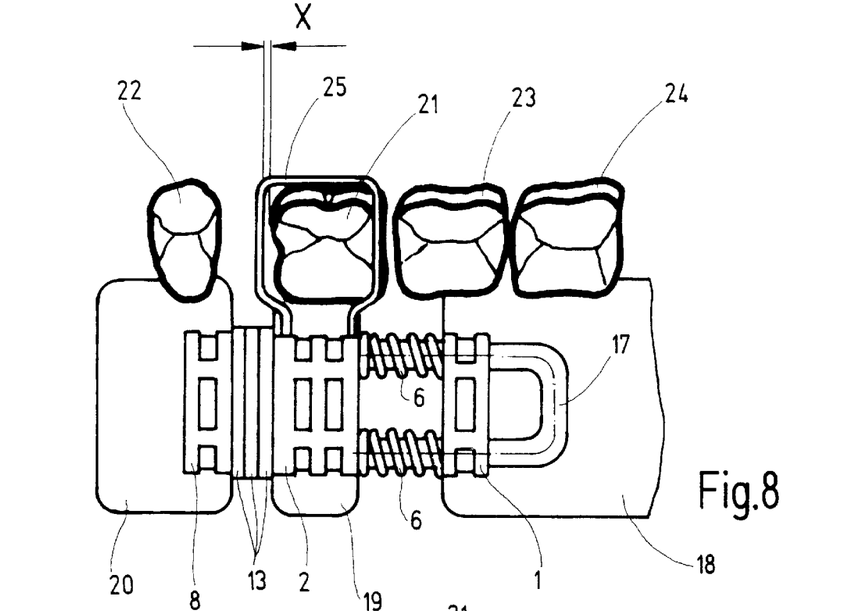
FIG. 8 shows the elastic expansion appliance of FIG. 5 before its "slide" is fastened onto a tooth.
Figure 9:
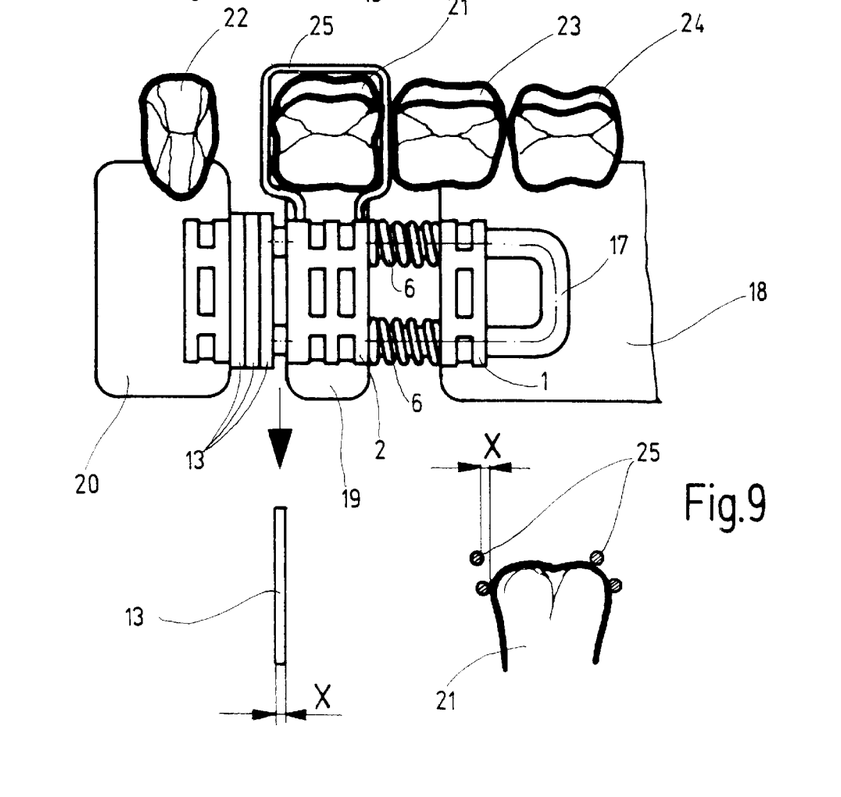
FIG. 9 shows the elastic expansion appliance of FIG. 8 after its slide is fastened onto a tooth.

The elastic expansion appliance depicted in FIGS. 4 through 6 has a field of application corresponding to a combined tension and compression screw according to Heller, it has as linear guidance means a shackle 17, bent into a U-shape, on whose parallel arms a first member is arranged immovably, a second member 2 displaceably, and a third member 8 immovably. A coiled spring 6 is slid onto each arm 3 and 4, and is arranged between first member 1 and second member 2. Arranged between second member 2 and third member 8, which serves as an immovable stop, is an adjustable-length stop 7 which comprises a stack of plate-shaped spacers 13 which are placed onto arms 3 and 4 transversely to their longitudinal direction, and for that purpose have two slots 14 next to one another. Similarly to the case with the first exemplifying embodiment, the plate-shaped spacers 13 each have, on an extension projecting beyond members 2 and 8, a hole 15 so that the plate-shaped spacers can he pulled off. For easier handling, the extensions having holes 15 are arranged at an offset from one plate 13 to the next, as depicted in FIGS. 5 and 6. FIGS. 8 and 9 show how the elastic expansion appliance depicted in FIGS. 4 through 6 is used. Each of the three members 1, 2, and 8, equipped with retainers 16, is embedded into a separate plate 18, 19, and 20, respectively. These plates 18 through 20 are fastened to the dentition, specifically the center plate 19 to tooth 21 whose position is to be corrected, and plates 18 and 20 to teeth 22, 23, and 24, whose position is not to be corrected, but which provide the necessary retention for the elastic expansion appliance. A shackle 25, which is slid onto tooth 21 that is to be corrected, is anchored on center plate 19. For the purpose of correction, the desired distance X by which the position of tooth 21 is to be modified is first established by pulling out some of the plate-shaped spacers 13. The apparatus consisting of the elastic expansion appliance and the three plates 18 through 20 is then arranged in the dentition as depicted in FIG. 8, shackle 25 initially being at an offset X from tooth 21 that is to be corrected. By displacing slide 19 against the force of springs 6, shackle 25 is then slid exactly over tooth 21 and anchored thereon (FIG. 9). Tooth 21 is subsequently displaced over the distance X by the springs that have been loaded in this fashion. A further plate-shaped spacer 12 can then, if necessary, be pulled out in order to change the position of tooth 21 further, if springs 6 are, as preferred pseudoelastic, the spring force effecting the correction remains almost constant during the correction.

Figure 7:
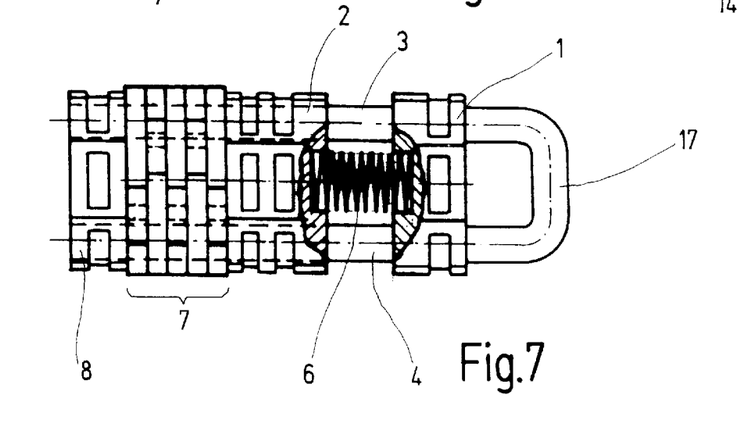
FIG. 7 shows a modified elastic expansion appliance in a plan view.

The elastic expansion appliance depicted in FIG. 7 differs from the elastic expansion appliance depicted in FIGS. 4 through 6 only in that instead of two springs it contains only one spring 6, which is not slid onto shackle 17 but is arranged centeredly.

In the two expansion appliances depicted, the locations of stop 7 and of springs 6 can be exchanged with one another.

Figure 10:
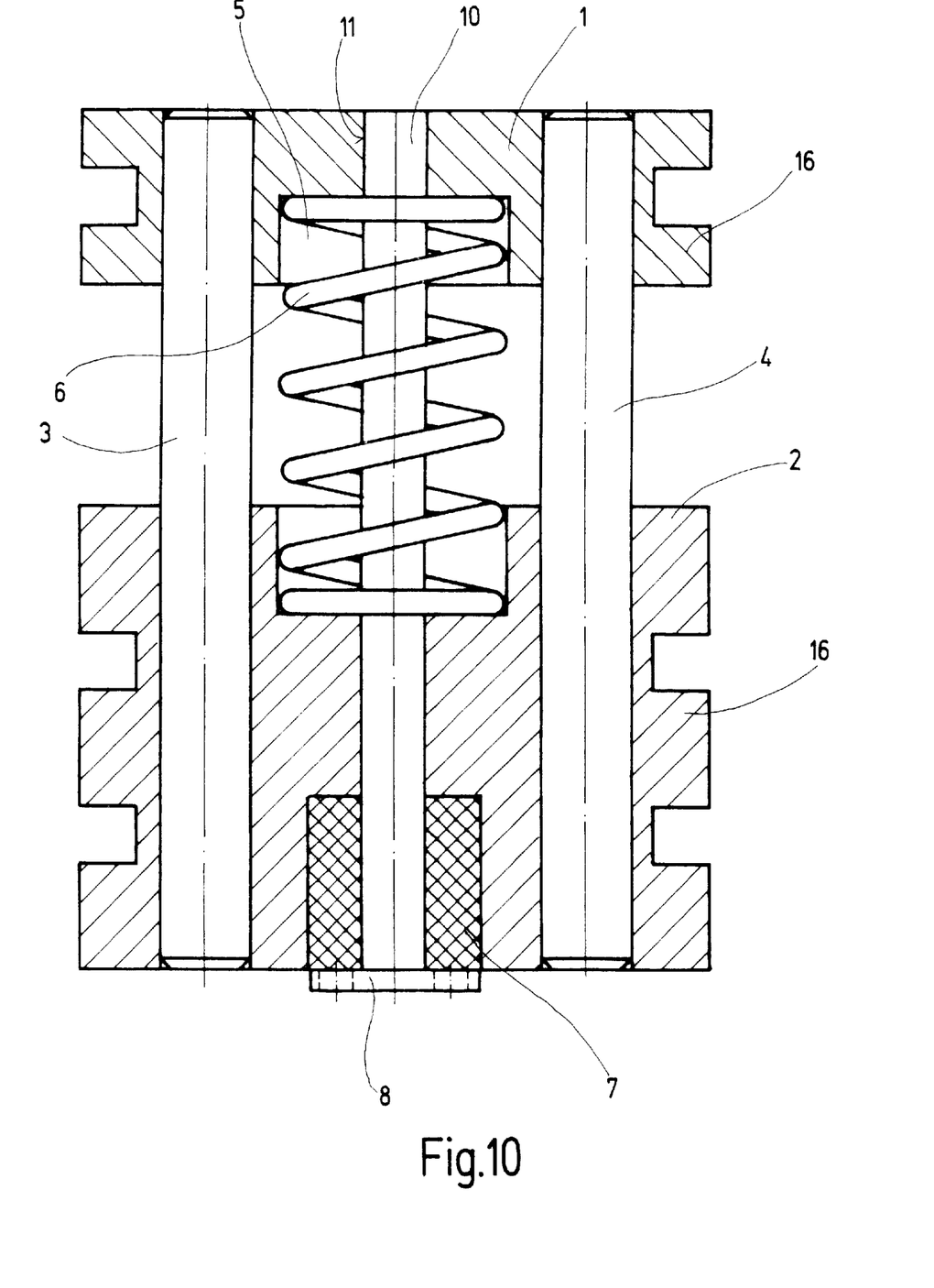
FIG. 10 shows, in a longitudinal section, an elastic expansion appliance for transverse expansions having a buttress made of a dissolving material.

FIG. 10 shows an elastic expansion appliance which differs from the one depicted in FIGS. 1 through 3 essentially in that the variable-length stop 7 is constituted not by a stack of plate-shaped spacers 13 but by a ring made of a material which gradually dissolves in the mouth, which is exposed to saliva through immovable stop B (which is immovable with respect to first member 1) that is of perforated configuration, and gradually dissolves from the end resting against immovable stop 8 and thus becomes shorter, leading to a gradual elongation of the displacement travel by which the spacing between the two members 1 and 2 can be increased.

Figure 11:
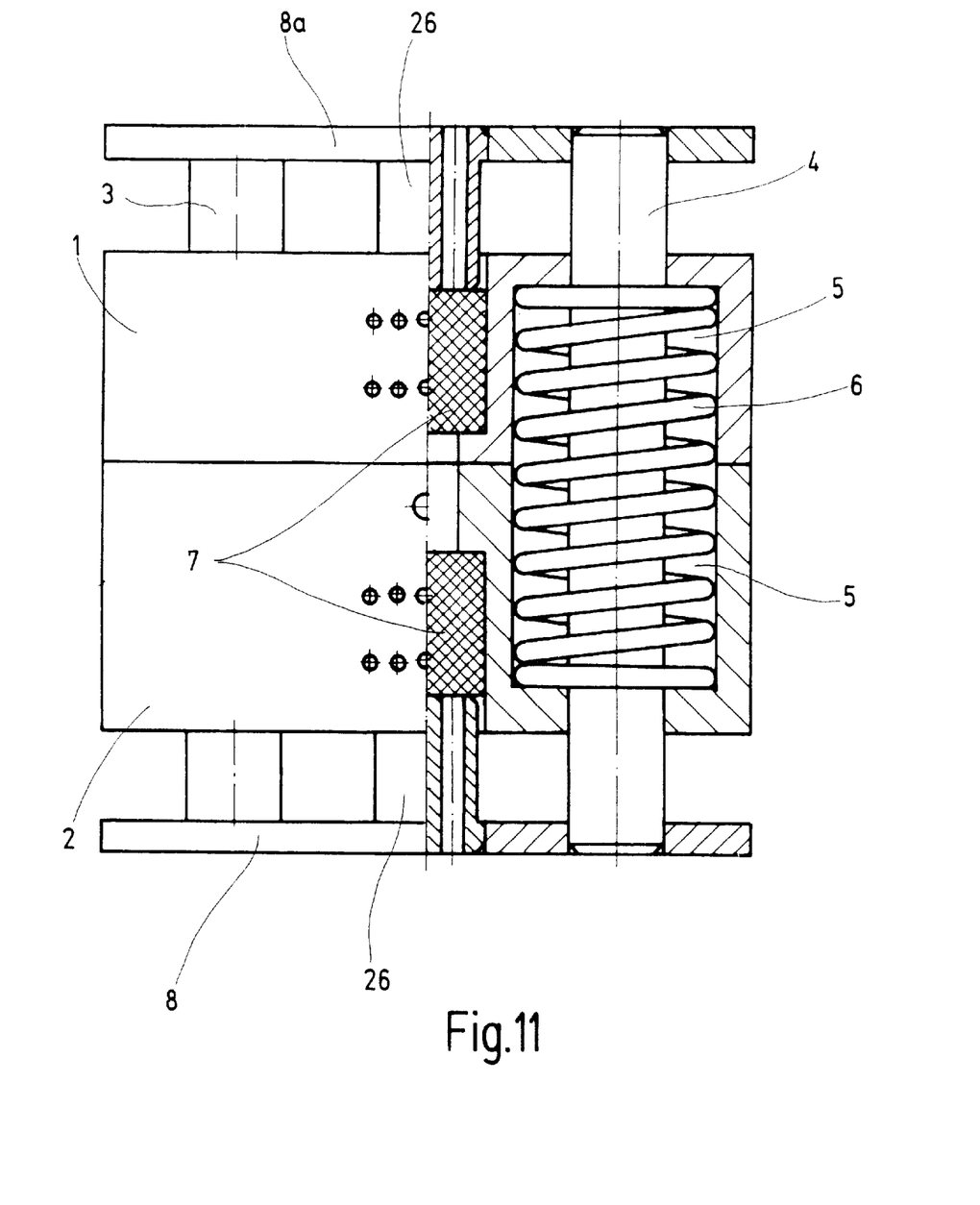
FIG. 11 shows an elastic expansion appliance for transverse expansions having two springs and two dissolving buttresses, half in longitudinal section and half in plan view.

The exemplifying embodiment depicted in FIG. 11 differs from the exemplifying embodiment depicted in FIG. 10 in that not just one central spring is provided but rather two springs 6 which surround the two guide rods 3 and 4 on whose ends two immovable stops 8 and 8a are fastened. Springs 6 push the two members 1 and 2 apart toward immovable stops 8 and 8a to the degree allowed by variable-length stops 7, made of dissolving material that are provided between immovable stops 8 and 8a and members 1 and 2. Dissolution occurs from the ends, via longitudinally through-perforated plungers 26 which proceed from immovable stops 8, 8a and are directed toward the dissolving stops 7.

Figure 12:
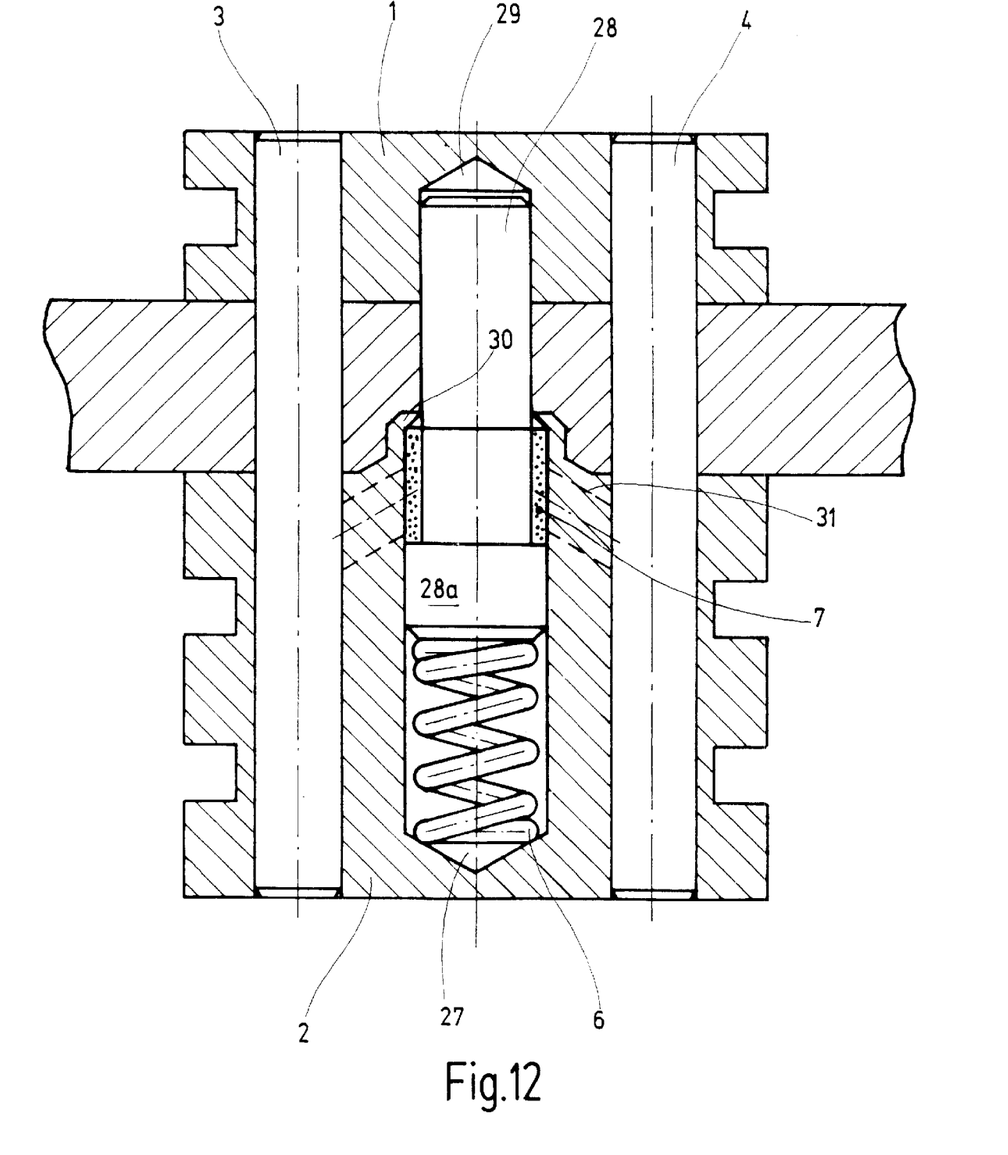
FIG. 12 shows, in a longitudinal section, an elastic expansion appliance for transverse expansions also having a buttress made of dissolving material.

The elastic expansion appliance depicted in FIG. 12 differs from the elastic expansion appliance depicted in FIG.

10 in that spring 6 is not retained directly between the two members 1 and 2, but rather is located in an orifice 27 of the one member 2 and presses on head 28a of a plunger 28 which is arranged with its head 28a in orifice 27 of member 2 and extents with its shaft into a blind hole 20 which is provided in the other member 1. The distance over which plunger 28 can be pushed out of orifice 17 is limited by a stop 7 which surrounds the shaft of plunger 28 in the vicinity of its head 28a over a certain length, and comes to a stop against the crimped-over rim 30 of orifice 27. Passages 31 in member 2 lead to the enveloping surface of the stop made of dissolving material. Through these passages, saliva can act on the material and result in a gradual dissolution of the stop, thus gradually increasing the distance over which the elastic expansion appliance can expand.

Figure 13:
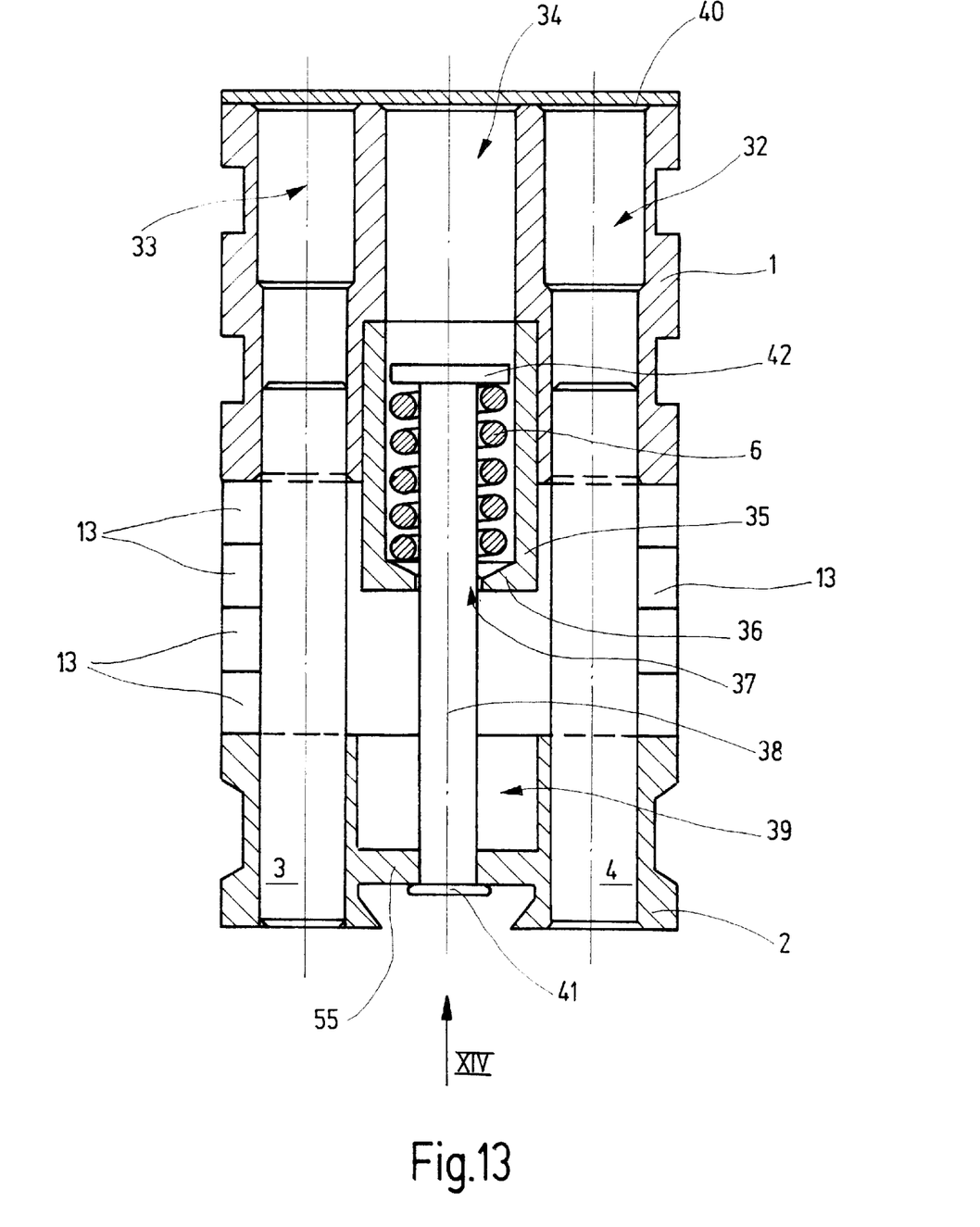
FIG. 13 shows a further exemplifying embodiment of an elastic expansion appliance in a horizontal section.
Figure 14:
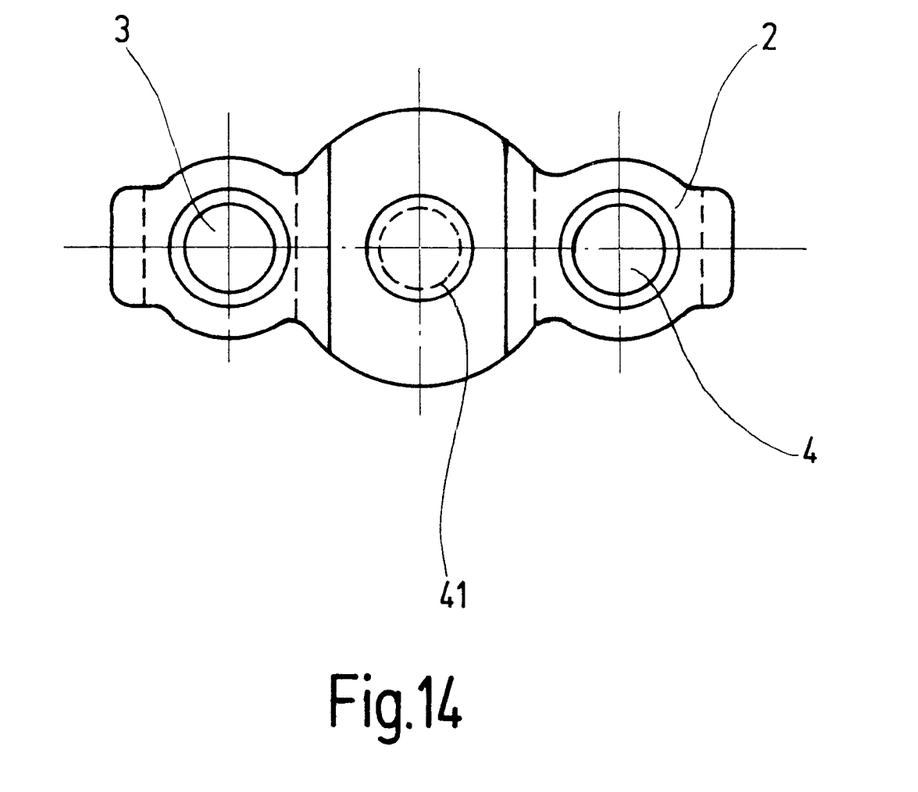
FIG. 14 shows view XIV of the elastic expansion appliance of FIG. 12.

The elastic expansion appliance depicted in FIGS. 13 and 14 has a first member 1 end a second member 2 which are connected via parallel guide rods 3 and 4 which sit immovably in second member 2, whereas first member i is displaceable on guide rods 3 and 4. Between orifices 32 and 33 which receive guide rods 3 and 4, there is located in first member 1 a central orifice 34 in which a cage 35 is fastened, for example by being pressed in. Cage 35 is a cylindrical sleeve which is open toward the back and has at its front end an end wall 36 which is equipped with a central orifice 37 through which a tie rod 38 is passed. A front section of cage 35 projects beyond first member 1. Second member 2 has a matching cylindrical recess 39 which is open toward cage 35. The projecting section of cage 35 can be introduced into recess 39.

The rear-side openings of orifices 32, 33 and 34 are closed off by a cover 40 fastened on first member 1.

Tie rod 38 has at each of its two ends an enlargement 40, 41. With the one enlargement 41, tie rod 38 makes contact against the exterior of wall 55 of second member 2 which delimits recess 39. A coiled spring 6 is retained between end wall 36 and second enlargement 42. Located between the two members 1 and 2 are plate-shaped spacers 13, preferably made of plastic, which are placed onto guide rods 3 and 4 in a manner corresponding to that in the exemplifying embodiments shown in FIGS. 4 through 9. These spacers 13 are not depicted in FIG. 15.

Spring 6 is installed in the stressed state. Because of its return force, it attempts to pull second member 2, via tie rod 36, toward first member 1. If one of plate-shaped spacers 13 is removed from guide rods 3 and 4 by pulling, spring 6 can then pull member 1 toward member 2 by no more than the thickness of the pulled-out spacer 13. FIG. 13 depicts, for example, four plate shaped spacers. After the third of them has been pulled out, cage 35 begins to move into recess 39 in contradistinction to the previous examples, in the exemplifying embodiment according to FIGS. 13 and 14 a negative elongation occurs, i.e. the two members 1 and 2 are brought closer to one another as the treatment of the teeth progresses.

Figure 15:
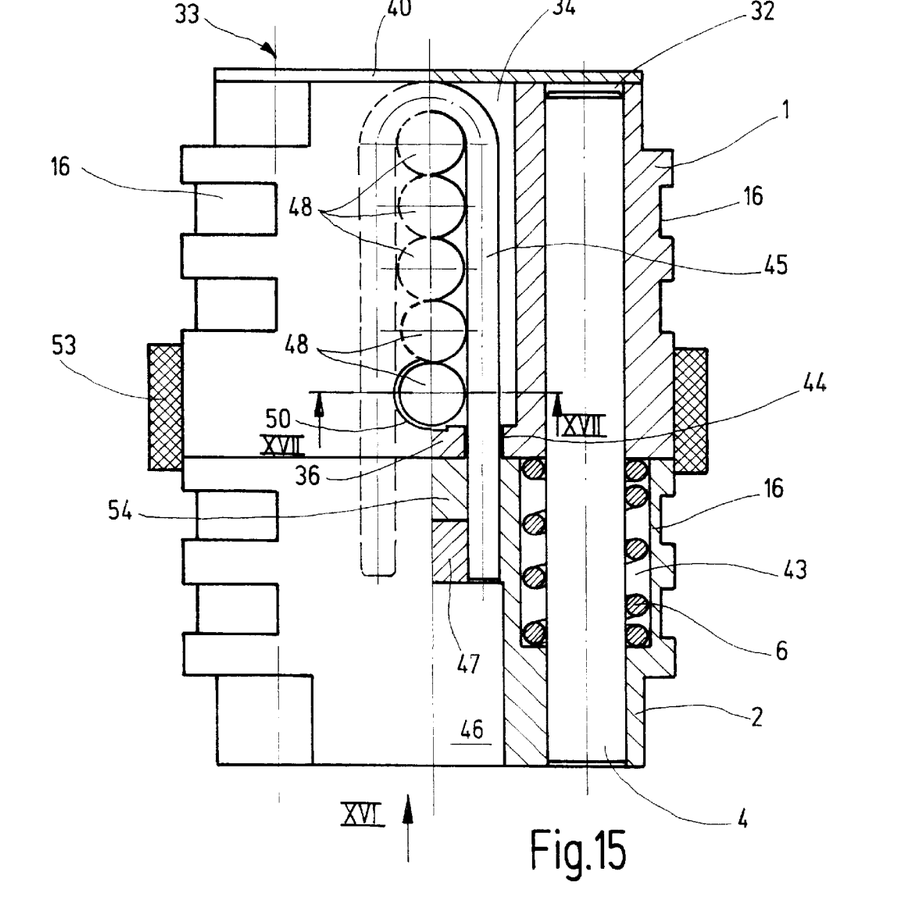
FIG. 15 shows a further exemplifying embodiment of an elastic expansion appliance in a horizontal longitudinal section (half-section)
Figure 16:
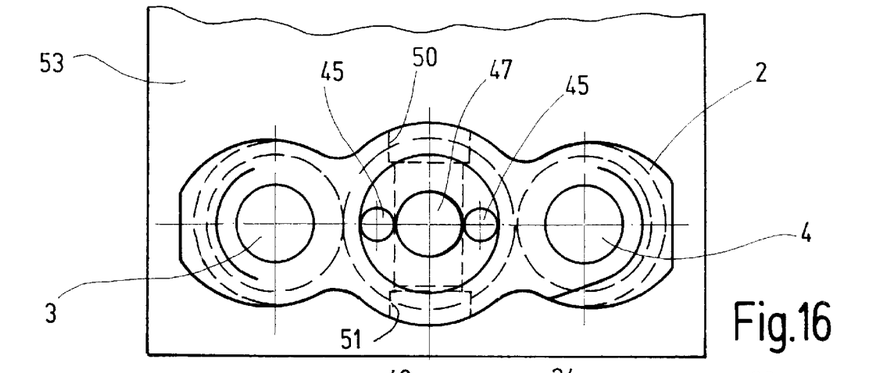
FIG. 16 shows view XVI of the elastic expansion appliance of FIG. 15.
Figure 17:
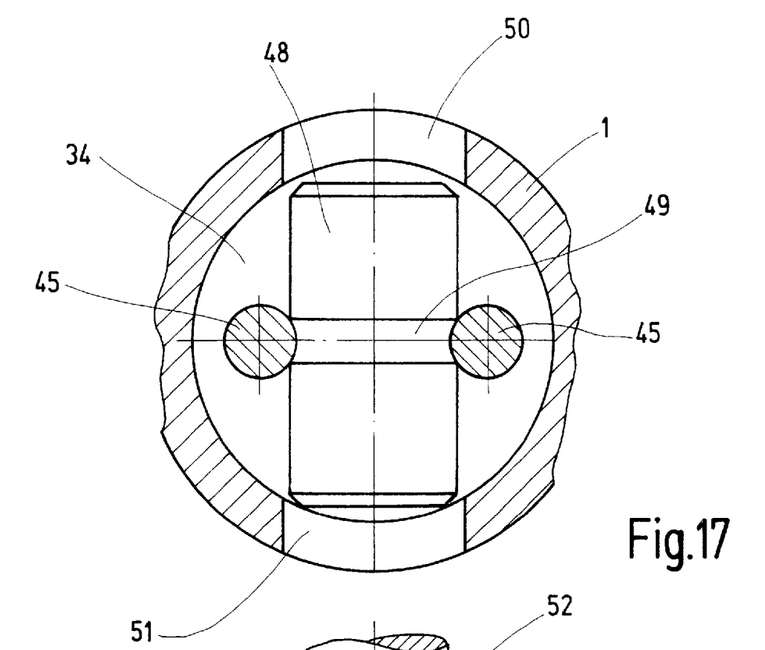
FIG. 17 shows a vertical partial section along section line XVII—XVII in FIG. 15.

In the exemplifying embodiment depicted in FIGS. 15 through 18, the elastic expansion appliance comprises a first member 1 and a second member 2 which are connected to one another by two guide rods 3 and 4 which sit immovably in second member 2, whereas first member 1 is displaceable on guide rods 3 and 4. In second member 2, the orifices which receive guide rods 3 and 4 ate widened in a section 43 adjoining first member 1, and each receive a coiled spring 6, only one of which is depicted in FIG. 15 because the elastic expansion appliance is depicted in a half-section. Located in first member 1 between the two orifices 32 and 33 which receive guide rods 3 and 4 is a larger central orifice 34.

Orifices 32, 33, and 34 are, as in FIG. 12, closed off by a cover 40. Orifice 34 does not pass through, but rather is a blind hole. Its end wall 36 has, in a diagonal arrangement, two smaller orifices 44 whose axes lie in the same plane as the axes of guide rods 3 and 4 and sitting in the two orifices 44 are the two arms of a U-shaped shackle 45 whose ends pass through an end wall 54 of second member 2 which faces first member 1. The ends of U-shaped shackle 45 are fastened in a recess 46 behind end wall 54 of second member 2 by the fact that a circular washer 47 is jammed between them and immobilized by calking.

When the two member 1 and 2 are resting against one snottier, as depicted in FIG. 15, shackle extends to cover 40. A plurality of cylindrical, rod-shaped spacers 48 is arranged in a row in shackle 45 in such a way that they lie with their enveloping surfaces parallel to one another. Cylindrical spacers 48 are preferably identical to one another and have at the center a constriction 49 with which they can be snapped in between the two arms of shackle 45, for which purpose the shackle is set into orifice 34 with some lateral clearance, so that it can be slightly widened elastically for the purpose of snapping in spacers 48.

Figure 18:
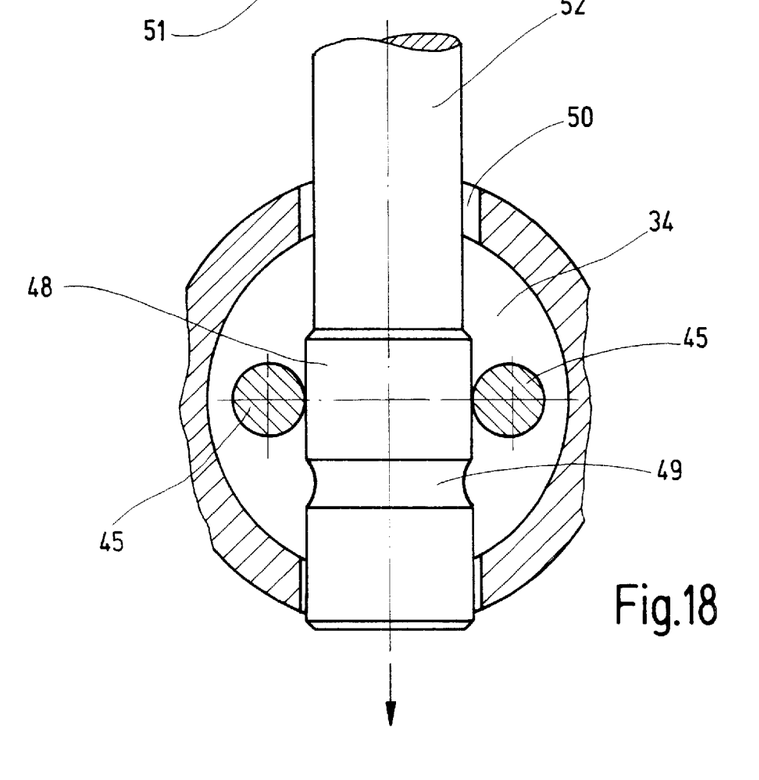
FIG. 18 shows, in a partial section corresponding to FIG. 17, the manner in which a rod-shaped spacer can be pushed out of the elastic expansion appliance.

Cylindrical orifices 50 and 51 are located in member 1, respectively at its upper side and lower side, only indirectly adjacent to end wall 36. The two orifices 50 and 51 align with one another and have a somewhat greater diameter than cylindrical spacers 48. The arrangement is such that a space 48 resting against and wall 36 between the arms of shackle 45 is in alignment with orifices 51 and 50. This makes it possible to push it out of the elastic expansion appliance using a rod 52 (FIG. 18). When this is done, springs 6, which are initially compressed (FIG. 15) can move members 1 and 2 away from one another by the thickness of one spacer 48, until the next of spacers 18 comes into contact against end wall 36.

In order to prevent pourable plastic from flowing into orifices 50 and 51 when the elastic expansion appliance is embedded into a plastic palate plate, a cover part 53 (FIGS. 15 and 16) made of plastic is first slid onto the elastic expansion appliance. Cover part 53 is removed after the elastic expansion appliance is embedded into a palate plate. Orifices 50 and 51 ore then open so that a cylindrical spacer 48 lying behind them can be pulled out as necessary, for which purpose shackle 45 is temporarily widened in order to release the snap lock.

As depicted in FIG. 14, a U-shaped shackle is preferred for holding and guiding spacers 48. It would also be possible, however, to provide only an L-shaped shackle, and to utilize for further guidance of spacers 48 the inner wall of central orifice 34 facing toward the shackle.

In all the exemplifying embodiments, the springs are preferably made of a pseudoelastic alloy.

What is claimed is:

1. An elastic expansion appliance for correcting misalignments of teeth, which has two members (1, 2), connected by linear guidance means (3, 4), the spacing between which can be modified via a spring (6) arranged between them, wherein in order to adjust the distance over which the spacing of the two members (1, 2) can be modified, a stop (7) of variable length (measured in the direction of the linear guidance means) is provided for the spring (6) or for a spring arrangement comprising more than one spring (6), and/or for one of the two members (1, 2).

2. The elastic expansion appliance as defined in claim 1, wherein the modifiable stop (7) is arranged between one of the members (2) and a fixed stop (8).

3. The elastic expansion appliance as defined in claim 1, wherein the spring(s) (6) are pseudoelastic.

4. The elastic expansion appliance as defined in claim 1, wherein the stop (7) is made entirely or partially of plastic.

5. The elastic expansion appliance as defined in claim 1, wherein the spring(s) (6) are arranged so that they attempt to increase the spacing between the two members (1, 2).

6. The elastic expansion appliance as defined in claim 1, wherein the spring(s) (6) are arranged so that they attempt to decrease the spacing between the two members (1, 2).

7. An elastic expansion appliance for correcting misalignments of teeth, which has two members (1, 2), connected by linear guidance means (3, 4), the spacing between which can be modified via a spring (6) arranged between them, wherein in order to adjust the distance over which the spacing of the two members (1, 2) can be modified, a stop (7) of variable length (measured in the direction of the linear guidance means) is provided for the spring (6) or for a spring arrangement comprising more than one spring (6), and/or for one of the two members (1, 2), the length of the stop (7) is modifiable only in steps.

8. The elastic expansion appliance as defined in claim 7, wherein the length of the stop (7) is modifiable only in steps of equal length.

9. The elastic expansion appliance as defined in claim 7, wherein the length of the stop (7) is modifiable in steps of unequal length.

10. An elastic expansion appliance for correcting misalignments of teeth, which has two members (1, 2), connected by linear guidance means (3, 4), the spacing between which can be modified via a spring (6) arranged between them wherein in order to adjust the distance over which the spacing of the two members (1, 2) can be modified, a stop (7) of variable length (measured in the direction of the linear guidance means) is provided for the spring (6) or for a spring arrangement comprising more than one spring (6), and/or for one of the two members (1, 2), a stack of spacers (13) is provided in order to constitute the stop (7).

11. The elastic expansion appliance as defined in claim 10, wherein the spacers (13) are configured in distinguishable fashion.

12. The elastic expansion appliance as defined in claim 11, wherein the spacers (13) are differently colored.

13. The elastic expansion appliance as defined in claim 10, wherein the spacers (13) are snap-locked to the linear guidance means (3, 4).

14. The elastic expansion appliance as defined in claim 10, wherein the spacers (13) are plate-shaped.

15. The elastic expansion appliance as defined in claim 10, wherein the spacers (13) are between 0.75 mm and 1.25 mm thick.

16. The elastic expansion appliance as defined in claim 10, wherein the spacers (13) are placed onto the linear guidance means (3, 4).

17. The elastic expansion appliance as defined in claim 16, the spacers (13) are placed onto the linear guidance means (3, 4) perpendicular to the longitudinal direction thereof, and for that purpose have a laterally open recess (14) into which the linear guidance means (3, 4) engage.

18. The elastic expansion appliance as defined in claim 10, wherein the spacers (13) can selectably be individually removed.

19. The elastic expansion appliance as defined in claim 10, wherein the spacers (48) are rod-shaped and are arranged between linear guidance means (3, 4; 45) in one of the members (1) and extend perpendicular to the linear guidance means (3, 4; 45), so that they can be pushed out of the elastic expansion appliance in their longitudinal direction.

20. The elastic expansion appliance as defined in claim 19, wherein the rod-shaped spacers (48) do not project beyond the member (1) in which they are arranged.

21. The elastic expansion appliance as defined in claim 19, wherein the spacers (48) are rods having a rectangular cross section.

22. The elastic expansion appliance as defined in claim 19, wherein the spacers (48) are cylindrical.

23. The elastic expansion appliance as defined in claim 19, wherein the spacers (48) are arranged in a recess (34) of the one member (1), in which recess (34) guidance means and/or holding means (45), which hold the spacers (48) in their selected orientation, are provided.

24. The elastic expansion appliance as defined in claim 19, wherein the spacers (48) have a constriction (49) at which they snap into the elastic expansion appliance.

25. The elastic expansion appliance as defined in claim 24, wherein the spacers (48) are held by a shackle (45) which is displaceable in the recess (34) of the one member (1) and is immobilized in the other member (2).

26. The elastic expansion appliance as defined in claim 25, wherein the shackle (45) is U-shaped.

27. The elastic expansion appliance as defined in claim 25, wherein the shackle (45) is circular in cross section.

28. The elastic expansion appliance as defined in claim 10, wherein the spring(s) (6) are pseudo elastic, and the spacers (13) are between 0.75 mm and 1.25 mm thick.

29. An elastic expansion appliance for correcting misalignments of teeth, which has two members (1, 2), connected by linear guidance means (3, 4), the spacing between which can be modified via a spring (6) arranged between them, wherein in order to adjust the distance over which the spacing of the two members (1, 2) can be modified, a stop (7) of variable length (measured in the direction of the linear guidance means) is provided for the spring (6) or for a spring arrangement comprising more than one spring (6), and/or for one of the two members (1, 2), the stop (7) is made of a substance which dissolves or decomposes in the mouth, so that the length of the stop automatically shortens in the mouth.

30. The elastic expansion appliance as defined in claim 29, wherein the elongated stop (7) is located in a sheath which is open only at one or both ends, but not along its periphery.

31. An elastic expansion appliance for correcting misalignments of teeth, which has two members (1, 2), connected by linear guidance means (3, 4), the spacing between which can be modified via a spring (6) arranged between them, wherein in order to adjust the distance over which the spacing of the two members (1, 2) can be modified, a stop (7) of variable length (measured in the direction of the linear guidance means) is provided for the spring (6) or for a spring arrangement comprising more than one spring (6), and/or for one of the two members (1, 2), the spring(s) (6) are arranged so that they attempt to decrease the spacing between the two members (1, 2), the spring (6) is retained in the one member (1) between a stop (36) provided immovably on that member (1) and a stop (42) that is displaceable in that member (1), the immovable stop (36) being closer to the other member (2) than the displaceable stop (42), and the displaceable stop (42) being connected via a tie rod (38) to the other member (2).

32. The elastic expansion appliance as defined in claim 31, wherein the spring (6) surrounds the tie rod (38).

33. The elastic expansion appliance as defined in claim 31, wherein the spring (6) is located in a cage (35) which is mounted immovably on the one member (1) and extends beyond that one member (1) toward the other member (2), which has a recess (39) into which the projecting part of the cage (35) can be introduced as the members (1, 2) approach one another.

* * * * *